United States Patent [19]

Goodwin et al.

[11] Patent Number: 4,758,421
[45] Date of Patent: Jul. 19, 1988

[54] BLEOMYCIN CONJUGATES AND METHOD

[75] Inventors: David A. Goodwin, Atherton; Claude F. Meares, Davis; C.-H Chang, Encinitas, all of Calif.

[73] Assignee: The Board of Trustees of the Leland Stanford Junior University, Stanford, Calif.

[21] Appl. No.: 712,377

[22] Filed: Mar. 15, 1985

[51] Int. Cl.$^4$ .................. A61K 43/00; A61K 37/02; A61K 33/24; C07K 7/00
[52] U.S. Cl. .................. 424/1.1; 424/131; 424/DIG. 6; 514/18; 514/53; 530/318
[58] Field of Search .............. 424/1.1, 131, 9, DIG. 6; 530/318; 514/18, 53

[56] References Cited

U.S. PATENT DOCUMENTS 4,043,998  8/1977  Meares et al. .................. 260/141
4,057,618 11/1977  Salmon et al. .................. 424/1.1
4,339,426  7/1982  Meares et al. .................. 424/1.1

OTHER PUBLICATIONS

C. H. Chang et al., *Biochem. and Biophys. Res. Comm.*, vol. 110, No. 3, 1983, pp. 959–966.
L. H. DeRiemer, *J. of Med. Chem.*, vol. 22, No. 9, pp. 1019–1023.
Goodwin, D. A., et al., *Radiology* (1970) 94:175–178.
Goodwin, D. A., et al., *IAEA* (1977) 2:61–69.
Begent, R. H. J., et al., *Lancet* (1982) 2:739–742.
Goodwin, D. A., et al., *J. Nucl. Med.* (1983) 24–31.
Goodwin, D. A., et al., *Eur. J. Nucl. Med.* (1983).
Wensel, T. G. and Meares, C. F., *Radioimmunoimaging and Radioimmunotherapy* (1983), pp. 185–196, Elsevier.
Strand, S-E., et al., *Radioimmunoimaging and Radioimmunotherapy* (1983), pp. 307–322, Elsevier.

*Primary Examiner*—John F. Terapane
*Assistant Examiner*—Virginia B. Caress
*Attorney, Agent, or Firm*—Ciotti & Murashige, Irell & Manella

[57] ABSTRACT

A bleomycin conjugate for use in targeting a compound to a body tumor. The conjugate includes an oxidized bleomycin/cobalt(III) complex and the compound to be targeted joined to the complex through a monodentate cobalt/sulfur coordinate bond. Also disclosed are methods for preparing the conjugate, and for targeting the compound to a body tumor, for purposes of tumor radioimaging or therapy.

21 Claims, 2 Drawing Sheets

BLEOMYCIN CONJUGATES AND METHOD

This invention was made with Government support under Grant Nos. CA-28343, CA-00462 and CA-16861 awarded by the National Institutes of Health. The Government has certain rights in this invention.

BACKGROUND AND SUMMARY

1. Field of the Invention

The present invention relates to tumor targeting, and particularly to novel bleomycin conjugates for targeting a radioimaging or therapeutic compound to a body tumor.

2. References

The following references are referred to herein by corresponding number:

1. Umezawa, H., *Pure Appl Chem* (1970) 28: 665.
2. Fujii, A., J., *Antibiot* (1973) 26: 398.
3. Nouel, J. P., et al, *Nouv Presse Med* (1972) 2: 95.
4. Goodwin, D. A., et al, *Seminars in Nuc Med* (1976) VI: 3.
5. Goodwin, D. A. et al, *In Radiopharmaceuticals II* Proceedings of the Second International Conference on Rad, N. Y., Sodd, V. J., et al, eds, (1979) pp 275-284.
6. Goodwin, D. A., et al, *J Nuc Med* (1981) 22: (9): 787.
7. De Riemer, L. H., et al, *J Med Chem* (1979) 22: 1019.
8. De Riemer, L. H., et al, *J Lab Comps & Radpharm* (1981) 18(10): 1517.
9. Wensel, T. G., et al, in *Radioimaging and Radioimmunotherapy*, Burchiel, S. W., et al, eds, Elsevier, (1983) p 185
10. Chang, C.-H., et al, *Biochem, Biophys Res Commun* (1983) 110(3): 959.
11. Kohler, B., et al, *Nature* (1975) 256: 495.
12. *Monoclonal Antibodies,* Kennett, T. J., et al, eds Plenum (1980).
13. Meares, C. F., et al, *Proc Natl Acad Sci (USA)* (1976) 73(11): 3803.

3. Background

Bleomycin is an anti-tumor antibiotic which has been shown to localize selectively within many types of tumors (References 1 and 2). Addition of $^{57}$Co to bleomycin yields a stable cobalt chelate whose use in radioimaging has been investigated (Reference 3). Although the chelate has been shown to provide good radioimaging capabilities, the relatively long half life of $^{57}$Co (270 days) creates unacceptable health and contamination problems. Other metal chelates of bleomycin, including $^{111}$In, $^{64}$Cu, $^{67}$Cu, $^{99}$Tc, $^{62}$Zn and $^{67}$Ga, that have been investigated lack the requisite in vivo stability for use in radioimaging (Reference 4).

The inventors have previously described a class of bleomycin-chelate compounds that can form stable metal chelates with a variety of metals, including $^{111}$In, that are clinically useful for radioimaging purposes. To prepare these compounds, an A$_2$ form of bleomycin is isolated from a commercial preparation of bleomycin, which characteristically contains a mixture of bleomycin A$_2$, B$_2$, and minor amounts of demethylated A$_2$ (DMA$_2$). The isolated A$_2$ form is demethylated to produce a thioether, which can react with a bifunctional chelating agent, such as p-bromoacetamidobenzyl-EDTA, to link the chelate to bleomycin through a sulfonium group. In vivo studies with model tumor systems in mice and with human cancer patients have demonstrated that the chelate compounds provide a useful radioimaging tool for determining size and location of many types of tumors (References 5-7).

The above-described bleomycin-chelate compounds, despite their demonstrated clinical usefulness in an experimental setting, have a number of practical limitations. The required bleomycin purification and demethylation steps mentioned above reduce product yield significantly and add to the overall preparation effort. The demethylation reaction may also lead to undesired side reactions (Reference 8). In terms of compound stability in vivo, it appears likely that the sulfonium group in the compound can be cleaved intracellularly, concurrently transferring the metal-chelate group to biomolecules in vivo, as evidenced by increased background levels in radioimaging applications.

4. Summary of the Invention

It is therefore an important object of the present invention to provide novel bleomycin conjugates which overcome above-discussed limitations of prior art bleomycin compounds.

A more specific object of the invention is to provide such conjugates which can be prepared readily and at high yields from commercially available bleomycin preparations.

Another object is to provide such conjugates which are stable in vivo, and have uptake and biodistribution characteristics which are substantially the same as those of cobalt bleomycin.

Providing a method of making such conjugates, and for using the same in tumor diagnosis and therapy are other important objects of the invention.

The invention includes a bleomycin conjugate for use in targeting a compound to a body tumor. The conjugate comprises an oxidized bleomycin/cobalt(III) complex and the compound to be targeted, joined to the complex through a monodentate cobalt-sulfur coordinate bond. The bleomycin/cobalt(III) complex may include one or more bleomycin forms, including A$_2$, DMA$_2$ and B$_2$ forms. In one general embodiment, the target compound is a chelating agent, with or without chelated metal, where the metal may be one which is useful for radioimaging or for therapeutic uses, either by itself or as a radiosensitizer (to be used with externally administered high-energy radiation). In another general embodiment, the compound is an anti-tumor drug or other therapeutic agent. The therapeutic compound may be joined to the bleomycin complex through a spacer arm having a labile bond, such as a disulfide bond, which can be cleaved intracellularly to release the drug from bleomycin after uptake into a tumor cell.

In a preferred method for forming the conjugate, an oxidized bleomycin-cobalt(III)-aquo complex is coupled, through a monodentate cobalt-sulfur coordinate bond, to a bifunctional thiol coupling agent. The target compound is attached to the complex through the free reactive end group of the coupling agent. The coupling agent thus forms a spacer arm between its coordinate-bond attachment to the bleomycin complex and the target compound.

The conjugate has tumor uptake and biodistribution characteristics which are very similar to those of cobalt bleomycin. Tumor-specific uptake can be enhanced severalfold by administering an antibody against the target compound prior to or contemporaneously with administering the conjugate to a patient. The enhanced tumor uptake appears to be due to the ability of antibody to sequester the relatively small conjugate in the bloodstream, and thereby prevent rapid renal clearance.

Further included in the invention are methods for using the novel conjugates for tumor radioimaging, therapeutic and radiosensitizing purposes.

These and other objects and features of the invention will become more fully apparent when the following detailed description of the invention is read in conjunction with the accompanying figures.

DETAILED DESCRIPTION OF THE INVENTION

I. Synthesis of Bleomycin Conjugates

Figure 1:
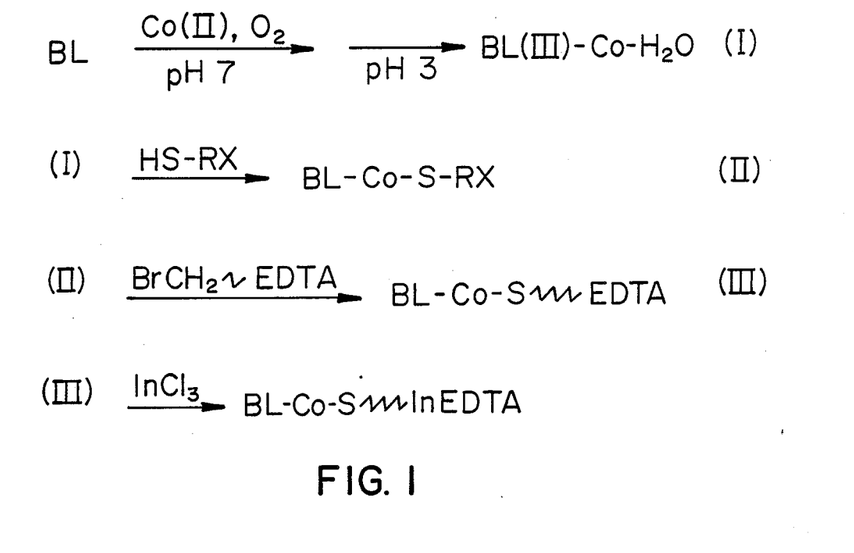
FIG. 1 shows a generalized reaction scheme for forming the conjugate of the invention.

A general reaction scheme for synthesizing bleomycin conjugates according to the present invention is shown in FIG. 1. The basic bleomycin (BL) structure has an R-group side chain characteristic of one of a number of known bleomycin forms. A typical bleomycin preparation includes a mixture of bleomycin $A_2$ (R=NH—$(CH_2)_3$—$S^+$—$(CH_3)_2$), DMA$_2$(R=N-H—$(CH_2)_3$—S—$CH_3$) and $B_2$ (R=NH—$(CH_2)_4$—NH-C—$(NH_2)_2^+$). As indicated above, previous bleomycin-chelate conjugate compounds which have been proposed previously by the inventors are formed by covalently attaching a reactive chelate directly to the thioether sulfur of demethylated bleomycin $A_2$, a procedure which necessitates both purification and demethylation steps. According to an important feature of the present invention, attachment of a target compound (compound to be targeted to a body tumor) to form a bleomycin conjugate involves coordination bonding of the target compound to cobalt in an oxidized bleomycin/cobalt complex, and is thus independent of the bleomycin R-group form.

Oxidized bleomycin cobalt complex, abbreviated herein as BL—Co(III), is prepared by mixing bleomycin with a divalent cobalt salt, such as $CoCl_2$, in the presence of oxygen. Initial incubation at pH 7.0 produces a mixture of both BL—Co—(III)—$H_2O$ and BL—Co(III)—$O_2H$, where the water and hydroperoxide groups are bound to the oxidized cobalt through a coordinate bond. The BL—Co(III)—$O_2H$ species in the Bl—Co(III) mixture can be converted to the BL—Co(III)—$H_2O$ species by incubating the mixture at a lowered pH, e.g. pH 3-4. Example I below describes the preparation of BL—Co(III)—$H_2O$ from commercial bleomycin.

An important feature of the preparation method is the displacement of an exogenous sixth ligand group, such as $H_2O$, from a BL—Co(III) complex by a sulfur-group anion to form a stable monodentate Co(III)—sulfur coordinate bond. As the terms are used, herein, "monodentate" refers to a single exogenous ligand and "coordinate" refers to the stable exogenous ligand bond. Although the preparation methods are described particularly with respect to displacement of $H_2O$ in a BL—Co(III)—$H_2O$, complex, it will be appreciated that other BL—Co(III) species containing suitable exogenous sixth-ligand anions which can be displaced by sulfur are suitable.

With reference to FIG. 1, BL—Co(III)—$H_2O$ is reacted with a thiol coupling reagent under conditions which lead to reversible replacement of cobalt-bound water by a sulfur anion, and formation of a new bleomycin—Co—(III)—S—complex. As indicated in FIG. 1, the coupling agent has the general form SH—RX where R is a spacer arm of selected length, solubility, and chain lability, depending on desired size, solubility and functional characteristics which the chain is to contribute to the bleomycin-target compound conjugate. The coupling agent's X group is a reactive functional group, such as a sulfhydryl, hydroxy, carboxy, amino, or hydroxysuccinimide group, which is capable of reacting through one of a variety of coupling reactions, with a suitable chemical group carried on a target compound, to covalently attach the target compound to the free end of the coupling agent. Preferred coupling agents used in forming bleomycin-EDTA conjugates described specifically herein include linear alkyldithiol reagents, such as 1,4-butanedithiol and dithiothreitol. Reactions for attaching these two compounds to BL—Co(III)—$H_2O$ are described below in Examples II and III, respectively.

Where the target compound for some applications is one which is preferably released from bleomycin, after uptake of the bleomycin-target compound conjugate into a tumor cell, the spacer arm may be constructed to contain a bond which is susceptible to intracellular cleavage. Disulfide and peptide bonds and certain sugar linkages are representative of bonds that may be cleaved intracellularly, and coupling agents containing these bonds may be advantageously employed. Example VII below illustrates the preparation of a bleomycin-EDTA conjugate with a spacer arm having an internal disulfide bond.

The target compound in the conjugate of the invention is a drug or other functional moiety which is to be targeted to a body tumor for tumor diagnosis or therapy. In several of the embodiments described herein, the target compound is a chelating agent, adapted to bind one of a variety of selected metals which may be a radionuclide useful in tumor radioimaging or tumor therapy, or a nonradioactive metal which is capable, in chelated form, of producing cytotoxicity, either by itself or as a radiosensitizer in conjunction with high-energy radiation. Various applications of metal-chelate target compounds will be considered in Sections III and IV below.

The target compound includes, or is modified to include, a functional group through which the compound can be coupled covalently to the free end functional group of the bleomycin-bound coupling agent.

The variety of functional groups mentioned with reference to the coupling agent's end group also apply to the compound's functional group. In a preferred embodiment of the invention containing a dithiol coupling agent, the target compound is prepared to include a sulfhydryl-reactive group, such as a bromoacetamide or iodoalkyl group, which readily forms a thioether bond between the target compound and coupling agent (FIG. 1, line 3). Examples IV and VI below illustrate the coupling of p-bromoacetamidobenzyl-EDTA to bleomycin/butanedithiol and bleomycin/dithiothreitol complexes, respectively. Example V illustrates the coupling of 6-bromohexanamidobenzyl EDTA to bleomycin/butanedithiol. The reactive chelate compounds are representative of compounds referred to as bifunctional chelating agents, so-called because the compounds contain both a metal-binding site and a reactive functional group capable of reacting with a suitable chemical group to produce coupling thereto (Reference 9).

Alternatively, the coupling agent may first be attached to the target compound, and subsequently coupled to the bleomycin-bound cobalt through a cobalt-sulfur bond to form the conjugate of the invention. And in some cases, the target compound itself may contain a reactive thiol group through which the compound can be coupled directly to the bleomycin-bound cobalt. A separate coupling reagent will generally be useful, however, to provide chemical group and steric features requisite for coupling the target compound to bleomycin-bound cobalt.

In a bleomycin conjugate which includes a chelating agent target compound, the conjugate is further treated to form a selected metal chelate. Although the metal may be attached to the chelating agent prior to coupling the latter to bleomycin, it is generally preferable, particularly with radionuclides having short half lives, to bind the metal to the conjugate shortly before its in vivo use. Exemplary metals which are useful for tumor diagnostic and therapeutic purposes are discussed in Sections III and IV below.

The selected metal is attached to the bleomycin-chelate conjugate (or unconjugated chelating agent) in a solution of the metal salt, preferably with mixing (FIG. 1, line 4). The metal-containing conjugate may be sterilized, e.g. by filtration, before in vivo use. Example VIII below illustrates the formation of an BL—Co—S—EDTA—$^{111}$In conjugate formed by incubating the BL—Co—S—EDTA conjugate from Example IV with $^{111}$InCl$_3$.

II. Tumor and Organ Uptake

This section examines the tumor and organ uptake characteristics of the bleomycin conjugate of the invention. The studies described herein show that the conjugate is very similar to cobalt bleomycin in its tumor uptake and biodistribution characteristics. This result is important in view of observed differences in tumor uptake and biodistribution between cobalt bleomycin and earlier proposed types of bleomycinchelate conjugate compounds. The section also describes a novel approach to increasing tumor uptake levels of a bleomycin conjugate, for purposes of enhancing tumor radioimaging or therapeutic uses of the conjugate.

Studies to determine tumor uptake and biodistribution of the bleomycin conjugate of the invention were carried out substantially according to methods described in Reference 8. Three groups of six mice each were prepared with KHJJ adenocarcinoma tumor implants in the flank. The mice in each group were injected in the tail veins with 1 to 2 mCi of (1) the bleomycin conjugate (BL—Co—S—EDTA—$^{111}$In) formed in accordance with Example VIII; (2) a previously described bleomycin A$_2$—EDTA—$^{111}$In compound (BLEDTA—II) formed according to Reference 8; or (3) bleomycin A$_2$—$^{57}$Co(III), the latter compound being a bleomycin—Co chelate having an exogenous sixth ligand, e.g., H$_2$O (Reference 10). Twenty four hours after the initial injections, the mice were sacrificed and tissue from the tumor and the various organs listed below in Table I were extracted, according to the procedures of Reference 8. Levels of $^{111}$In and $^{57}$Co in the extracts were measured and calculated in terms of percent initial dose per gram tissue. The results for each of the three compounds examined are shown in Table I. The righthand column gives tumor to organ uptake ratios (T/O) for the BL—Co—S—EDTA—conjugate.

TABLE I

|  | BLEDTA-II | $^{57}$Co—BLA$_2$ | BL—Co—S—EDTA | T/O |
|---|---|---|---|---|
| Blood | 0.42 ± .13 | 0.06 ± .01 | 0.04 ± .004 | [7.1] |
| Heart | 0.20 ± .04 | 0.11 ± .01 | 0.05 ± .005 | [6.0] |
| Lungs | 0.44 ± .06 | 0.14 ± .02 | 0.09 ± .01 | [3.1] |
| Liver | 0.37 ± .08 | 0.28 ± .03 | 0.19 ± .02 | [1.5] |
| Spleen | 0.34 ± .05 | 0.07 ± .01 | 0.16 + .02 | [1.8] |
| Kidney | 2.23 ± .46 | 1.04 ± .13 | 0.92 ± .17 | [0.3] |
| Tumor | 0.90 + .19 | 0.38 ± .12 | 0.28 ± .04 |  |
| Muscle | 0.07 ± .02 | 0.02 ± .005 | 0.02 ± .002 | [17] |
| Bone | 0.17 ± .01 | 0.02 ± .003 | 0.10 + .01 | [2.9] |
| Skin | 0.17 ± .01 | 0.05 ± .01 | 0.04 ± .01 | [6.6] |
| Gut | 0.10 ± .04 | 0.08 ± .02 | 0.11 ± .08 | [4.0] |

As seen from the data, uptake levels of BL—Co(III)—S—EDTA—$^{111}$In are quite similar to those of bleomycin—$^{57}$Co. Interestingly, the BL—Co(III)—S—EDTA—$^{111}$In compound more closely follows bleomycin—$^{57}$Co than it does the BLEDTA—II compound also studied. One explanation for this finding is suggested by earlier studies by the inventors showing that an appreciable portion of radioactivity from intravenously injected BLEDTA-II becomes stably attached to white blood cells (neutrophil granulocytes), presumably due to chemical reactivity of the compound, resulting in alkylation of biomolecules by the reactive metal-chelate group. While the Co(III)—S coordinate bond in the conjugate of the present invention may be subject to some dissociation in vivo, BL—Co—S—EDTA does not act as an alkylating agent to label other molecules. Thus, it produces lower background levels of radioactivity. Additionally, the BLEDTA—II compound is formed under conditions which produce an unusual Co(III) ligand bonding to the bleomycin A$_2$ side chains. This complex may very well have tumor uptake properties which are different from those of bleomycin complexes having exogenous Co ligands. In any event, the nature of the exogenous sixth ligand group (H$_2$O of BL—$^{57}$Co and S—EDTA—$^{111}$In for BL—Co—S—EDTA—$^{111}$) appears not to have an important effect on bleomycin tumor uptake and biodistribution.

The BL—Co—S—EDTA—$^{111}$In conjugate employed in the above study contains an EDTA conjugate linked to bleomycin through a butane coupling arm. The effect on biodistribution of a more hydrophilic coupling arm (threitol) and the partially uncharged chelate Indium N-(2-hydroxyethyl)ethylenediaminetriacetate (In—HED3A) was also examined. Four conjugates having various combinations of a butane or threitol coupling arm, and an EDTA or HED3A chelating group were formed. (See example II and III for preparation methods involving butane and threitol coupling arms, respectively). The four compounds all showed similar $^{111}$In biodistribution in mice, supporting the argument above that the nature of the sixth ligand exogenous group on bleomycin-Co does not have a large effect on its biodistribution.

From the studies on mice reported above, and from earlier studies on biodistribution and excretion of bleomycins in mice and in human patients, it is known that bleomycins, including the conjugates of the present invention, have circulation half lives in the bloodstream of roughly an hour. The rapid clearance of intravenously administered bleomycins contributes to the relatively low uptake levels, expressed in percent dosage per gram tissue, observed in the mice studies reported above. The remainder of this section describes a novel approach to extending the blood circulation time of bleomycin conjugates, to effect as much as a 10-30 fold increase in tumor uptake of bleomycin conjugates.

Broadly, the approach involves preparing an antibody against the whole conjugate, or either the bleomycin or target-compound components of the conjugate, and administering the antibody to the patient either prior to or contemporaneous with administration of the bleomycin conjugate. The antibody is preferably a monoclonal antibody that recognizes and binds to the target compound, with the latter coupled to bleomycin. Such antibodies may be commercially available for some target compounds which are selected. For other target compounds, antigen-specific monoclonal antibodies may be made by somatic cell hybridization techniques described originally by Kohler and Milstein (Reference 11) and reviewed at length in Reference 12.

Monoclonal antibodies against L—benzyl—EDTA—In were prepared in cooperation with Hybritech, Inc., 11085 Toneyana Road, San Diego, Calif. 92121. Briefly, an L—benzyl—EDTA—In isothiocyanate reagent was reacted with keyhole limpet hemocyanin, which was used to immunize mice. Splenocytes derived from the immunized mice were fused with a suitable tumor cell line, using known somatic cell hybridization techniques. Promising clones were grown in mouse ascites fluid, and the antibodies obtained were purified by ion-exchange chromatography. Two antibodies against L—benzyl—EDTA—In, designated CHA255 and CHB235, were selected.

The binding constants of the two monoclonal antibodies with L—benzyl—EDTA chelates of several different metals were determined by equilibrium dialysis. The measured binding constants were shown in Table II below, with standard deviations indicated in parentheses.

TABLE II

| Metal | $K_b$(CHA255) | $K_b$(CHB235) |
|---|---|---|
| Sc (III) | $3.0 \times 10^6$ ($\pm 13\%$) | $5 \times 10^4$ ($\pm 39\%$) |
| Fe (III) | $1.8 \times 10^8$ ($\pm 13\%$) | $2.4 \times 10^6$ ($\pm 18\%$) |
| Ga (III) | $5 \times 10^5$ ($\pm 45\%$) | $5.2 \times 10^4$ ($\pm 16\%$) |
| In (III) | $4.0 \times 10^9$ ($\pm 6.9\%$) | $1.1 \times 10^8$ ($\pm 7.9\%$) |
| Tb (III) | $1.2 \times 10^6$ ($\pm 12\%$) | $2.7 \times 10^4$ ($\pm 15\%$) |
| Yb (III) | $1.1 \times 10^6$ ($\pm 20\%$) | $2 \times 10^4$ ($\pm 90\%$) |
| Mn (II) | $2.8 \times 10^6$ ($\pm 9.1\%$) | $2.8 \times 10^4$ ($\pm 24\%$) |
| Co (II) | $2 \times 10^6$ ($\pm 37\%$) | $9.4 \times 10^4$ ($\pm 22\%$) |
| Co (III) | $8 \times 10^5$ ($\pm 60\%$) | $<1 \times 10^4$ |
| Cu (II) | $1.7 \times 10^6$ ($\pm 12$) | $8.1 \times 10^4$ ($\pm 11\%$) |
| Zn (II) | $1.4 \times 10^6$ ($\pm 14\%$) | $3.5 \times 10^4$ ($\pm 27\%$) |
| Cd (II) | $1.5 \times 10^7$ ($\pm 8.0\%$) | $1.6 \times 10^5$ ($\pm 8.1\%$) |

The data show that each antibody is highly specific for the antibody-inducing antigen, L—benzyl—EDTA—In, having a binding constant that is between about 1 to 4 orders of magnitude greater than for nonantigen metal chelates.

Table III gives binding constant data from a second binding affinity study, involving different In—EDTA and In—HED3A chelates. As seen from the data, the two antibodies, and particularly the CHA255 antibody, show marked specificity for the L—benzyl—EDTA moiety of the antigen.

TABLE III

| Chelator | $K_b$(CHA255) | $K_b$(CHA235) |
|---|---|---|
| L-Benzyl—EDTA | $4.0 \times 10^9$ ($\pm 6.9\%$) | $1.1 \times 10^8$ ($\pm 7.9\%$) |
| D-Benzyl—EDTA | $6 \times 10^7$ ($\pm 40\%$) | $3.6 \times 10^7$ ($\pm 9.3\%$) |
| EDTA | $1.7 \times 10^8$ ($\pm 8.3\%$) | $1.3 \times 10^8$ ($\pm 13\%$) |
| HED3A | $4.2 \times 10^7$ ($\pm 12\%$) | $4.0 \times 10^7$ ($\pm 14\%$) |

The enhanced conjugate uptake produced by coadministration of antibody is seen in the following study, in which a group of six mice prepared with a KHJJ flank tumor, as described in the above tumor uptake study, was each injected with 1-2 mCi BL—S—Co—EDTA—$^{111}$In plus 10 μgram CHA255 antibody. After 24 hours, tumor and organ uptake levels were measured as described above. The results obtained, expressed as percent initial dose per gram tissue, are given in Table IV below. Data from Table I above on the biodistribution of BL—Co—S—EDTA—$^{111}$In (no antibody) are reproduced here for comparative purposes. Tumor to organ uptake ratios (T/O) for both regimens are also given.

TABLE IV

| | BL—Co—S—EDTA | T/O | Antibody (CHA255) + BL—Co—S—EDTA | T/O |
|---|---|---|---|---|
| Blood | .04 ± .004 | 7.1 | 4.32 ± 1.03 | 1.4 |
| Heart | 0.05 ± .005 | 6.0 | 1.05 ± .23 | 5.8 |
| Lungs | 0.09 ± .01 | 3.1 | 2.12 ± .51 | 2.9 |
| Liver | 0.19 ± .02 | 1.5 | 2.17 ± .62 | 2.8 |
| Spleen | 0.16 ± .02 | 1.8 | 1.00 ± .21 | 6.1 |
| Kidney | 0.92 ± .17 | 0.3 | 1.81 ± .30 | 3.4 |
| Tumor | 0.28 ± .04 | | 6.10 ± 1.13 | |
| Muscle | 0.02 ± .002 | 1.7 | 0.34 ± .05 | 18.2 |
| Bone | 0.10 ± .01 | 2.9 | 0.60 ± .10 | 10.2 |
| Skin | 0.04 ± .01 | 6.6 | 0.70 ± .17 | 8.8 |
| Gut | 0.11 ± .08 | 4.0 | 0.75 ± .18 | 8.4 |

The data show that administration of the antibody contemporaneously with the bleomycin conjugate enhanced tumor uptake, over bleomycin conjugate alone, about 30 fold (6.10% vs. 0.28%). An approximately tenfold enhancement in tumor uptake was seen when the CHB235 antibody was administered.

A similar enhancement in tumor uptake was observed when the CHA255 antibody was co-administered with the bleomycin—EDTA—$^{111}$In compound described earlier by the inventors in Reference 6, demonstrating that the antibody-enhancement effect can be generalized to bleomycin-target compound conjugates having quite diverse structures.

The amount of antibody administered in the above study corresponds to an antibody concentration in the bloodstream of about $5 \times 10^{-8}$M. Similar studies performed in support of the present invention indicate that amounts of intravenously administered antibody (CHB235), up to calculated bloodstream concentration values of about $10^{-7}$M, produced increased tumor uptake levels without altering tumor/organ uptake levels appreciably. Above an antibody concentration of about $10^{-7}$M, the distribution of bleomycin conjugate became skewed toward distributions observed for covalently labeled circulating antibodies, suggesting a greater influence of the antibodies themselves, and a reduced influence of bleomycin, in determining conjugate distribution. At antibody levels below a calculated bloodstream concentration, of about $10^{-8}$M, only relatively modest increases in tumor uptake were observed. The optional concentration of antibody will depend in part on the $K_b$ of the antibody/antigen complex. For antibodies that have $K_b$ values appreciably less than the $10^8$–$10^9$ values of the CHA235, CHA255 antibodies, optional antibody blood concentrations will be correspondingly greater. Similarly, at lower binding constants, optional antibody concentrations will be correspondingly greater. Optional enzyme bloodstream concentrations may typically range between about $10^{-13}$ to $10^{-5}$M, depending on the $K_b$ value.

An explanation of the data just presented is that the added circulating antibodies serve as a bloodstream reservoir for the bleomycin conjugate, maintaining the concentration of free bleomycin in the bloodstream at a level determined by the dissociation constant of the antibody/conjugate pair (e.g., about $10^{-8}$M), and thereby preventing rapid clearance of free conjugate. At low antibody concentrations the antibody "reservoir" is insufficient to sequester a significant portion of the conjugate in the bloodstream, and rapid clearance and low tumor uptake levels result. At high antibody concentrations, the conjugate tends to be cleared with the antibody, as evidenced by biodistribution that resembles antibody clearance by the reticuloendothelial system.

The antibody may be added to the conjugate before administration, to form a stable antibody-bound bleomycin-conjugate composition. Alternatively, the antibody/bleomycin composition may be formed in vivo, by administering the antibody prior to conjugate administration.

Figure 2:
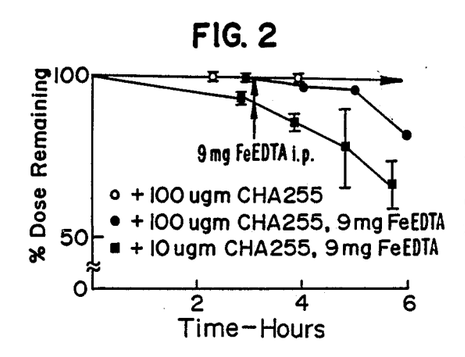
FIG. 2 is a plot showing the effect of a flushing dose of FeEDTA on the retention of a bleomycin EDTA conjugate coadministered with an anti-EDTA antibody.

The advantage of enhanced tumor uptake of the bleomycin conjugate, produced by co-administration of an antibody may be partially offset by (1) higher background levels of radioactivity in some non-tumor tissues, and (2) greater total patient exposure to the conjugate, e.g., greater radiation exposure in the case of a conjugate having a chelated radionuclide. A regimen which was found to take advantage of the increased tumor uptake of antibody administration, yet minimize non-specific uptake effects due to increased body retention, involves first co-administering the conjugate and antibody, and after maximal or near-maximal tumor uptake has occurred, flushing the conjugate from the patient with an intravenously administered dose of non-toxic antigen capable of competing with the bleomycin conjugate for binding to the antibody. By way of illustration, BL—S—Co—$^{111}$In and either 10 μg or 100 μg CHA255 antibody were administered to each of a group of mice, as described above. Three hours later, the mice were each injected with 9 mg FeEDTA intraperitoneally. FIG. 2 shows that whole body levels of $^{111}$In drop about 20% in the three-hour period after administering the flushing dose of FeEDTA. By contrast, the $^{111}$In whole body level remains nearly unchanged without the flushing treatment. Thus, reversible antibody/bleomycin-target complexes can serve as carrier systems to increase target compound concentrations in the patient, but also allow flushing of the target compound from the blood and whole body after tumor concentrations of the target compound have reached maximum levels. This combined regimen produces higher tumor-to-blood ratios of the target compound, and in the case of a radionuclide-containing conjugate, lower patient exposure by flushing of radioactivity from the body through the kidneys. The increase in quality of whole-body imaging which is achieved by the combination of antibody administration followed by flushing dose of competing antigen is seen from a comparison of FIGS. 3A and 3B, to be described in the next section.

III. Radioimaging

One of the significant uses of the conjugate of the invention is in radioimaging body tumors. In this application, a bleomycin-radionuclide-chelate conjugate is injected into a patient and allowed to localize in tumor region(s). These regions are imaged using radioimaging equipment, such as a gamma camera, single-photon emission computed tomograph, or a position emission computed tomograph.

The conjugate chelating agent is one capable of binding a selected radionuclide with high affinity under physiological conditions, typically a polyaminocarboxylic acid such as EDTA, HED3A and diethylenetriaminepentaacetic acid (DTPA), and related compounds. Various radionuclides have been used in imaging applications including $^{67}$Cu, $^{67}$Ga, $^{68}$Ga, $^{72}$As, $^{89}$Zr, $^{97}$Ru, $^{55}$Co, $^{99m}$Tc, and $^{111}$In. A preferred radionuclide is $^{111}$In, whose relatively short half life (about 3 days) minimizes contamination and toxicity problems, but provides detectable signals after a localization period of a few days.

The conjugate is administered to the patient in manner that will provide efficient uptake in the suspected tumor region(s). Intravenous administration is typically used, at a dose of between about 1 to 2 mCi radionuclide. Antibody against the target compound, at a dose calculated to produce a blood concentration, for example, between about $10^{-8}$–$10^{-7}$M, may be administered prior to or contemporaneous with the conjugate, to enhance conjugate uptake by the tumor, as described in Section II. Preferably the antibody treatment is followed by a flushing dose of a non-radioactive antigen capable of competing with the bleomycin conjugate for binding to the antibody.

Figure 3A:
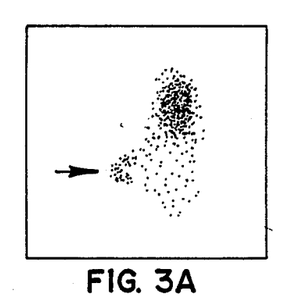
FIGS. 3A and 3B are representations of whole-body scans of a tumor-bearing animal 3 hours after administration of a bleomycin-EDTA-$^{111}$In conjugate and anti-EDTA antibody (FIG. 3A), and 4 hours after administration of a flushing dose of FeEDTA (FIG. 3B), where the dark areas show regions of $^{111}$In concentration.
Figure 3B:
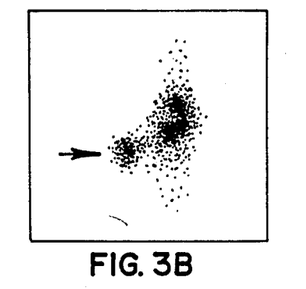

To illustrate the radioimaging method, a mouse prepared with a KHJJ flank tumor, as described above, was injected with 1-2 mCi BL—S—Co—EDTA—$^{111}$In plus 100 μg of CHA255 antibody. Three hours after the initial bleomycin conjugate administration, a whole-body scan, using computer digitation of the whole-body image, was performed on the animals. The image is shown in FIG. 3A, where the tumor region is indicated by the arrow. Also three hours after the initial bleomycin administration, a 9 mg dose of FeEDTA was given to the animal, to increase renal clearance of the bleomycin conjugate and reduce conjugate background levels. Four hours after administration of the flushing dose of FeEDTA, a whole-body scan of the animal was made, with the results shown in FIG. 3B. As seen from a comparison of the two figures, the quality of whole-body images was markedly improved four hours after the flushing dose, with an increase in contrast between tumor and background. The increased concentration of bleomycin conjugate in the kidneys in the FIG. 3B image can be seen.

IV. Therapeutic Uses

Several factors discussed above suggest advantages of the bleomycin conjugates for tumor therapy: The conjugates can be formed with a variety of therapeutic drug or metal-chelate target compounds; the conjugates localize preferentially in tumor tissue; and uptake levels may be increased dramatically by coadministration of a conjugate-specific antibody. In this section another important factor—the ability of therapeutic bleomycin conjugates to produce tumor-cell toxicity, or to enhance the cytotoxic effects of radiation—will be considered.

The target compound in the therapeutic conjugate may be a conventional anti-cancer drug, such as a DNA alkylating or crosslinking agent, or an antimetabolite, where the drug is coupled to a bleomycin-bound coupling agent through a reactive funtionality, as discussed in Section I. Another general class of therapeutic compounds are radiotherapeutic agents including radionuclides, such as $^{90}Y$, $^{197}Hg$, and $^{67}Cu$ which can bind to bleomycin-linked chelating agents, and radioactive elements such as $^{131}I$ which can be coupled to amino acids or the like for attachment to bleomycin through a suitable coupling arm. Non-radioactive metal chelates such as iron, copper or ruthenium chelates, which produce cytotoxic effects through redox mechanisms, and which can also potentiate the cytotoxic action of radiation on cells are another class of therapeutic agents suitable in the present invention.

As an example of the latter class, the ability of a bleomycin-FeEDTA conjugate to produce selective cytotoxicity in cultured tumor cells was demonstrated. Chinese hamster ovary (CHO) cells were cultured in standard cell-culture medium, under log phase growth conditions. Increasing concentrations of either BL—Co—S—FeEDTA or FeEDTA were added to each of two groups of cells. The cells were incubated for 60 minutes at 37° C., and the percent cell survivors was determined conventionally by serial dilution in microtitre plates.

Figure 4:
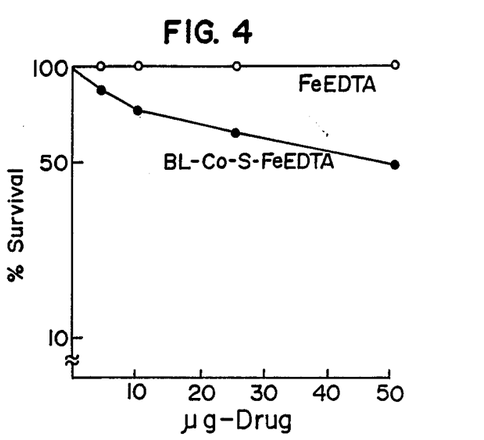
FIG. 4 is a plot showing survival of CHO cells exposed for 60 minutes to FeEDTA or to a bleomycin-FeEDTA conjugate.

The results are shown in FIG. 4. As seen, concentrations above about 25 μM BL—Co—S—FeEDTA conjugate produced significate cell toxicity (about 50% cell death at 50 μM conjugate drug), whereas FeEDTA was relatively non-toxic, even at higher dosages. In parallel tests cobalt-bleomycin was shown to be relatively nontoxic, although metal free bleomycin produced high toxicity. The results indicate that the cytotoxicity of FeEDTA is greatly enhanced in tumor cells by conjugation to bleomycin, presumably due to selective uptake of the iron chelate by the cells.

Figure 5:
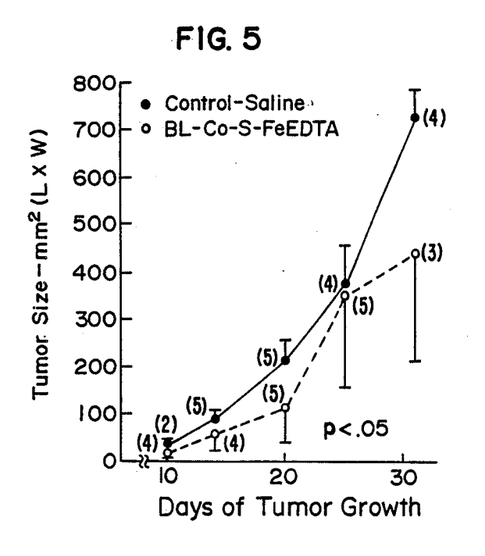
FIG. 5 is a plot showing changes in tumor sizes in animals treated with saline or a bleomycin-FeEDTA conjugate constructed according to the invention.

The effectiveness of a bleomycin-FeEDTA conjugate in reducing tumor growth was examined in two groups of C-57 black mice prepared with B-16 melanomas. One group of mice received daily injections of 3.6 mg/kg conjugate, given intravenously through the tail vein, and a second (control) group received an equivalent-volume of FeEDTA in saline, also administered intravenously each day. The tumor lengths and widths were measured daily to determine tumor area size (1×w). The measured tumor sizes, as a function of time are shown in the FIG. 5, where the numbers in parentheses indicates the number of animals studied in each group, and the vertical bars indicate standard variation within each group. As seen, the sizes of tumors in animals treated with the bleomycin-FeEDTA conjugate were generally smaller than in control animals and statistically smaller ($p<0.05$) at day 20.

Considering now the use of a bleomycin-conjugate for radiosensitization, this application relys on the ability of the conjugate to potentiate the cell-destructive effects of high-energy radiation. One useful gauge of radiosensitization is provided by the extent of DNA nicking in vitro by high energy radiation, since DNA is the major target of radiation damage in vivo. In one in vitro study performed in support of the present invention, the extent of in vitro DNA nicking by gamma radiation in the presence and absence of a bleomycin-FeEDTA conjugate was examined. Supercoiled $\phi$x174 DNA was prepared to a final concentration of 34 μg DNA per ml, at pH 7.4, and the DNA solution was divided into 4 samples. The first sample, a control, received neither gamma radiation nor added iron-chelate conjugate. Sample 2 received a dose of about 24 kilorads of gamma irradiation from a $^{137}Cs$ gamma radiation source. To sample 3 was added the BL—Co—S—FeEDTA conjugate to a concentration of 5 μM, and the solution was gamma irradiated under the conditions applied to sample 2. Sample 4 was made 5 μM in BL—Co—S—FeEDTA as in Sample 3, but the solution was not irradiated.

Figure 6:
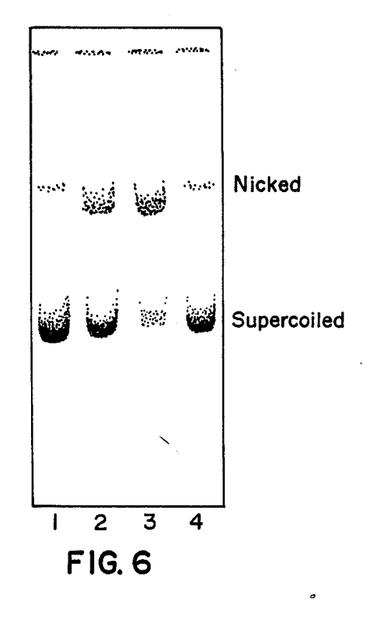
FIG. 6 shows an agarose gel electrophoresis pattern of supercoiled DNA before treatment (lane 1) and after treatment with radiation alone (lane 2), radiation plus a bleomycin-FeEDTA conjugate (lane 3) and the bleomycin-FeEDTA conjugate alone.

The DNA from the four samples was isolated by conventional means and size fractionated by agarose slab gel electrophoresis. The gel was stained with ethidium bromide, producing the gel pattern seen in FIG. 6, where lanes 1-4 correspond to samples 1-4, respectively. The upper bands correspond to nicked DNA, and the mid-position bands, to supercoiled DNA. As seen, only samples 2 and 3 showed appreciable amounts of nicked DNA. The relative precentages of coiled and nicked DNA in samples 2 and 3 was quantitated by gel densitometer scans. Approximately 40% of the material treated with gamma radiation alone was nicked (sample 2), whereas about 80% of the material treated with gamma radiation in the presence of BL—Co—S—FeEDTA (sample 3) was nicked.

The above study indicates the extent to which high energy radiation damage is enhanced by the iron-chelate conjugate. It can be appreciated that, in vivo, where the compound is localized in tumor tissue and where radiation can be focused selectively on the tumor, highly selective tumor cytotoxicity can be achieved. The conjugate is administered typically 18-24 hours before radiation treatment, preferably by intravenous injection. Antibody prepared against the conjugate may be coadministered, as described above, to increase conjugate uptake levels at the tumor site.

From the foregoing, it can be appreciated how various objects and features of the present invention are achieved. The novel conjugate is prepared by a simple high-yield procedure that utilizes coordinate rather than covalent, bonding to bleomycin. The coupling agent employed in the conjugate synthesis can be selected to achieve desired length, solubility and bond lability characteristics in the spacer arm connecting the target compound to the bleomycin. The coupling agent can further be designed for coupling to a variety of different reactive functional groups which may be available in target compounds.

The conjugate has been shown herein to have tumor uptake the biodistribution characteristics which are substantially identical to native bleomycin—Co, and these characteristics are relatively independent of the coupling agent and target compound used in forming the conjugate. The conjugate appears to have greater in vivo stability than earlier bleomycin conjugate compounds used by the inventors, and is thus expected to produce more satisfactory background levels in radiomaging and lower non-specific toxicity in therapeutic applications.

The use of antibodies in conjunction with the conjugates, to increase selective tumor uptake of the conjugates by an order of magnitude or more, provides a powerful therapeutic method for delivering target compounds selectively and at high levels to tumor tissue.

The following examples illustrate various aspects of preparing and using the conjugate of the invention, but are in no way intended to limit the scope thereof.

EXAMPLE I

Preparation of Bleomycin—Co(III)—H$_2$O

Blenoxane (bleomycin sulfate) was obtained from Bristol Laboratories (Syracuse, NY). A 50 ml aqueous solution of blenoxane (4 mM) and slight molar excess of CoCl$_2$ was adjusted to pH 7.0 with NaOH, and the mixture allowed to stand at room temperture overnight. The resulting greenish-brown solution, consisting of a mixture of bleomycin—Co(III)—H$_2$O and bleomycin—Co(III)—O$_2$H, was acidified to pH 3.0 with HCl, and incubated for 1 day at 37° to produce substantially complete conversion of the bleomycin—Co(III)—O$_2$H to bleomycin—Co(III)—H$_2$O (BL—Co—H$_2$O). The progress of the reactions was monitored by HPLC, as described in Reference 8. The solution was lyophilized and the residue was dissolved in 54 ml methanol. Undissolved material was removed by centrifugation.

EXAMPLE II

Coupling 1,4-butanedithiol to BL—Co—H$_2$O 1,4-butanedithiol was obtained from Aldrich Chemical Co. (Milwaukee, WI); BL—Co—H$_2$O was prepared as in Example I.

Six ml of 1,4-butanedithiol was added to the solution of BL—Co—H$_2$O in methanol and flushed with nitrogen gas. To the solution was added 1 ml triethylamine and the reaction was allowed to proceed to completion at room temperature (3 hours). The formation of bleomycin—Co—S—(CH$_2$)$_4$—SH was followed by HPLC, as monitored at 254 nm. If desired, the product can be isolated by preparative HPLC.

After centrifugation to remove precipitate formed during the reaction, the supernatant portion of the reaction mixture was evaporated to dryness. The dried material was dissolved in 40 ml H$_2$O and extracted several times with ether to remove residual 1,4-butanedithiol. The aqueous phase was again evaporated to dryness and the product taken up in water.

EXAMPLE III

Coupling Dithiothreitol to BL—Co—H$_2$O

Diothiothreitol, was obtained from Aldrich Chemical Co. (Wilwaukee, WI) and prepared as a 1M aqueous solution. A 10-fold molar excess of dithiothreitol was reacted with BL—Co—H$_2$O from Example I, in an aqueous reaction mixture made pH 8.5 with triethylamine. Reaction conditions were similar to those of Example II. Following completion of the reaction, unreacted dithiothreitol was removed by several extractions with ethylacetate.

The aqueous phase from the extraction was evaporated to dryness, to remove residual ethylacetate. The bleomycin—Co—S—CH$_2$—(CHOH)$_2$—CH$_2$—SH product was taken up in water.

EXAMPLE IV

Preparing a BL—Co—S—Butane—linked—EDTA Conjugate (S)-(p-bromoacetomidobenzyl)-EDTA (BABE-EDTA) was prepared according to the procedure detailed in Reference 8. BL—Co—S—(CH$_2$)$_4$—SH (135 μmol) from Example II was combined with a 10-fold molar excess of BAB—EDTA in a total aqueous volume of 15 ml, and the solution was adjusted to pH 8.2 with NaOH. The reaction was allowed to proceed at room temperature and was monitored by HPLC, substantially was described in Reference 8. The bleomycin-conjugate reaction product was eluted immediately from the system, whereas BL—Co—S—(CH$_2$)$_4$—SH was retained slightly.

The desired butane-linked bleomycin—Co(III)—thioacetomidobenzyl—EDTA (BL—Co—S—EDTA) conjugate was separated by ion-exchange chromotography using an A-25 ion exchange resin obtained from Pharmacia. The reaction mixture was applied to the column (1×45 cm), and the reaction first washed with 150 ml of 0.01M ammonium formate, pH 8.2, followed by a 500 ml gradient of 0.01M to 0.3M ammonium formate. The column wash and gradient steps were performed at 4° C., and product solution was monitored at 280 nm. Product eluted at about 0.2M ammonium formate. The pooled product fractions gave an overall product yield, as determined by absorbance at 292 nm, and based on an extinction coefficient of $2 \times 10^4$ M$^{-1}$ cm$^{-1}$, of about 20%. The product was examined by thin-layer chromatography (TLC) analysis on silica gel 60 obtained from Merck. The product showed only one spot, with R$_f$ of 0.7, when developed in 10% w/v aqueous ammonium acetate: methanol (1:1, v/v).

Proton ($^1$H) NMR spectra at 360 MHz showed two separate resonances for each of the two histadine protons in bleomycin, suggesting the existence of two separate species, perhaps involving a different arrangement of ligands around cobalt. Preliminary studies conducted in support of the invention indicate that the two species can be separated by HPLC.

EXAMPLE V

Preparation of BL—Co—S—Butane—linked—6—BABE EDTA Conjugate

An aqueous solution (1.5 ml; 3.0 mM) of the 1,4-butanedithiol adduct of cobalt-bleomycin (BL—Co—S—(CH$_2$)$_4$—SH) from Example II was mixed with an aqueous solution (0.1 ml; 50 mM) of 6-bromohexanoamidobenzyl EDTA (6-BABE). The pH was adjusted to 7.5-8.0 with concentrated sodium hydroxide (about 2 μl), and 80 μl of 0.2M sodium iodide solution was added to give a final concentration of 10 mM sodium iodide. The reaction vial was flushed with argon gas, covered with foil, and incubated at 37° C. for 1.5 hours. The reaction mixture was tested with dithionitrobenzoic acid to insure that all thiol groups had reacted. The BL—Co—S—EDTA product was isolated by HPLC on a 75×7.5 cm TSK DEAE-5-PW column using a concave gradient (#8 on Waters' Model 660 Solvent Programmer) of 0–2M ammonium acetate, pH 5.5 (flow rate: 1 ml/min; 20 min gradient). Three groups of peaks were collected, these having approximate retention times of 2–5 min, 11–16 min, and 22–26 mins. Thin layer chromatography (silica gel; 10% ammonium acetate/methanol (1:1)) using $^{57}$Co identified the components of these groups to be, respectively: Cobalt-bleomycin compounds without 6-BABE, Cobalt bleomycin compounds with 6-BABE (the desired product), and free chelate (6-BABE).

EXAMPLE VI

Preparation of Bl—Co—S—Dithiothreitol—linked—EDTA Conjugate

BL—Co—S—CH$_2$—(CHOH)$_2$—CH$_2$—SH from Example III was reacted with a 10-fold molar excess of BAB—EDTA under conditions similar to those in Example IV. The desired threitol-linked bleomycin—Co(III)—thioacetomidobenzyl—EDTA (BL—Co—S—EDTA) conjugate was purified as by ion exchange chromatography, using an ammonium formate gradient, as described in Example IV.

EXAMPLE VII

Preparation of a BL—Co—S—EDTA Conjugate with a Disulfide Link

An aqueous solution (2.0 ml, 3.0 mM) of the 1,4-butane-dithiol adduct of cobalt-bleomycin (BL—Co—S—(CH$_2$)$_4$—SH) from Example II was mixed with an aqueous solution (1.1 ml, 6.25 mM) of pyridyl—S-2—(CH$_2$)$_4$—S—acetamidobenzyl EDTA ("pyridyl chelate") and the resulting solution was incubated at 37° C. for one hour at which time analytical HPLC (C$_{18}$) showed the disappearance of the BL—Co—S—(CH$_2$)$_4$—SH peaks. The reaction mixture was applied (in 0.4–1.0 ml aliquots) to a 10×250 mm C$_{18}$ HPLC column and the products separated using a 30-minute linear gradient with 0.1M ammonium acetate, pH 7, and acetonitrile (90:10 to 40:60; flow rate: 4.5 ml/min). Five peaks were collected having from 2 to 12 minutes retention time. The desired product (the adduct of BL—Co—S—(CH$_2$)$_4$—SH and the "pyridyl chelate") was shown by $^{57}$Co TLC procedures to be present in the peak (actually a family of closely related peaks due to the presence of different bleomycin "terminal amine" groups) having a retention time of approximately 11 minutes.

Example VIII

Preparation of Bl—Co—S—EDTA—$^{111}$In

Carrier free $^{111}$InCl$_3$ was obtained from Medi-Physics, and purified as described in Reference 8. Fifty μl (1–2 mCi) InCl$_3$ in 0.01M HCl was added to an equal volume of 0.5 mM butane—linked BL—Co—S—EDTA from Example IV. After vortexing, the solution was neutralized with NaHCO$_3$. The BL—Co—S—EDTA—$^{111}$In compound showed a single spot with an R$_f$ of 0.4 when originally prepared from pure bleomycin A$_2$. When B$_2$ is also present, another spot whose the R$_f$ is 0.7 is also present.

While preferred embodiments of the invention have been described, it will be apparent that various changes may be made without departing from the spirit of the invention.

It is claimed:

1. A bleomycin conjugate comprising a bleomycin/-cobalt(III) complex joined through a cobalt-sulfur bond to a thiol coupling-agent containing an attached target compound.

2. The conjugate of claim 1, wherein the bleomycin complex is formed from a mixture of A$_2$, DMA$_2$ and B$_2$ forms.

3. The conjugate of claim 1, wherein said coupling agent is a dithiol agent which is attached to the target compound through a thioether linkage.

4. The conjugate of claim 3, wherein said coupling agent is 1,4 butanedithiol or dithiothreitol.

5. The conjugate of claim 1, wherein said coupling agent contains an internal bond which is susceptible to cleavage within a tumor cell.

6. The conjugate of claim 5, wherein said internal bond is a disulfide bond.

7. The conjugate of claim 6, wherein said coupling agent has the form: —S—CH$_2$—(CHR)$_n$—CH$_2$—S—S—CH$_2$—(CHR)$_n$—CH$_2$—S—, where R is H or OH, and n=2–5.

8. The conjugate of claim 1, wherein said target compound is a chelate compound.

9. The conjugate of claim 8, wherein said chelate compound is a parasubstituted 1-phenyl or 1-benzyl EDTA.

10. The conjugate of claim 8, for use in treating a tumor, wherein said chelate compound is a metal chelate of $^{90}$Y, $^{197}$Hg or $^{67}$Cu.

11. The conjugate of claim 8 for use in radioimaging a body tumor, wherein said chelate compound is a metal chelate of $^{111}$In, $^{67}$Ga, $^{68}$Ga, $^{64}$Cu, $^{99}$Tc, $^{67}$Cu, $^{197}$Hg, $^{97}$Ru, $^{57}$Co, $^{55}$Co, or $^{62}$Zn.

12. The conjugate of claim 8 for use in radiosensitizing a body tumor, wherein said chelate compound is a metal chelate of iron, copper or ruthenium.

13. A method of attaching a target compound to bleomycin comprising
mixing bleomycin and Co(II) in the presence of oxygen, and at a pH less than about 4, to form an oxidized bleomycin/cobalt(III)—H$_2$O complex, and
reacting the complex with a thiol coupling agent to which the target compound can also be attached.

14. The method of claim 13, wherein the bleomycin includes a mixture of A$_2$, DM A$_2$, and B$_2$ bleomycin forms.

15. A method of claim 13, wherein said reacting includes reacting the oxidized bleomycin-Co(III) complex with a bifunctional thiol coupling agent, to attach the agent to the complex through such cobalt/sulfur coordinate bond, and covalently coupling the compound to the coupling agent.

16. The method of claim 13, wherein said coupling agent is a dithiol reagent, and said reacting further includes reacting the target compound with the reaction product of said complex and coupling agent.

17. A method for radioimaging a body tumor comprising
providing a bleomycin-metal chelate conjugate composed of the bleomycin conjugate of claim 1, wherein said attached target compound is a radioimagable metal chelate compound,
injecting the conjugate into the body, to produce a localization of the conjugate within the tumor, and
imaging the distribution of such metal in the body.

18. The method of claim 17, wherein the metal-chelate compound is an $^{111}$In chelate of a parasubstituted 1-phenyl or 1-benzyl EDTA.

19. A method for radiosensitizing a body tumor, to enhance the cytotoxic effect of high-energy radiation on the tumor, comprising providing a bleomycin-metal chelate conjugate composed of the bleomycin conjugate of claim 1, wherein said attached target compound is metal-chelate compound capable of enhancing DNA nicking by such radiation, injecting the conjugate into the body to produce a localization of the conjugate within the tumor, and irradiating the tumor with such high energy radiation.

20. The method of claim 19, wherein the compound is an iron, copper or ruthenium chelate of a parasubstituted 1-phenyl or 1-benzyl EDTA.

21. A method of treating a tumor comprising providing a bleomycin-metal chelate conjugate composed of the bleomycin conjugate of claim 1, wherein said attached target compound is a metal-chelate compound capable of producing cytotoxic effects when taken up in tumor cells, and injecting the conjugate into the body to produce a localization of the conjugate within the tumor.

* * * * *